United States Patent
Coperet

(10) Patent No.: US 7,181,356 B2
(45) Date of Patent: Feb. 20, 2007

(54) DEVICE AND METHOD FOR ANALYZING THE STRUCTURE OF A MATERIAL

(75) Inventor: Philippe Coperet, Coupvray (FR)

(73) Assignee: Socomate International, Crecy la Chapelle (FR)

( * ) Notice: Subject to any disclaimer, the term of this patent is extended or adjusted under 35 U.S.C. 154(b) by 0 days.

(21) Appl. No.: 10/490,513

(22) PCT Filed: Sep. 26, 2002

(86) PCT No.: PCT/FR02/03283

§ 371 (c)(1),
(2), (4) Date: Sep. 1, 2005

(87) PCT Pub. No.: WO03/029808

PCT Pub. Date: Apr. 10, 2003

(65) Prior Publication Data

US 2004/0249589 A1    Dec. 9, 2004

(30) Foreign Application Priority Data

Sep. 28, 2001    (FR)    .................................. 01 12516

(51) Int. Cl.
*G01N 29/24*    (2006.01)

(52) U.S. Cl. .................... 702/91; 702/176; 702/36; 367/124; 367/125; 367/127; 367/129; 367/906; 367/907; 367/128; 73/625; 73/583

(58) Field of Classification Search .................... 79/91, 79/36, 176; 367/124, 125, 127, 128, 129, 367/906, 907; 73/572, 587, 603, 623, 592, 73/594, 577, 579, 583; 324/536, 509, 543, 324/242, 240, 220; 340/650
See application file for complete search history.

(56) References Cited

U.S. PATENT DOCUMENTS

| 3,936,791 | A | | 2/1976 | Kossoff | |
|---|---|---|---|---|---|
| 4,459,851 | A | * | 7/1984 | Crostack | ...................... 73/587 |
| 4,641,526 | A | * | 2/1987 | Izumi et al. | .................. 73/572 |

(Continued)

OTHER PUBLICATIONS

INPI Search Report (Exhibit 4).

*Primary Examiner*—Carol S. W. Tsai
(74) *Attorney, Agent, or Firm*—John P. White; Cooper & Dunham LLP

(57) ABSTRACT

The invention relates to a device that is used to analyse the structure of a material. The inventive device comprises: probe elements (5) which are used to (i) emit a wave, in the material, with emission delay laws that correspond to several simultaneous deviations and (ii) receive, on the different probe elements (5), signals from the refraction of said wave by the material; detection channels, each detection channel being connected to a probe element (5), in order to collect the refraction signals and to transmit same to data processing means (4); and delay circuits that apply a delay on each detection channel according to the reception delay laws which are predetermined and which correspond to the different deviations of the wave emitted. The invention also relates to an analysis method which can be used, in particular, on said device.

13 Claims, 3 Drawing Sheets

U.S. PATENT DOCUMENTS

| | | | |
|---|---|---|---|
| 4,835,478 A * | 5/1989 | Haddon et al. | 324/536 |
| 5,010,503 A * | 4/1991 | Paton et al. | 702/176 |
| 5,010,885 A * | 4/1991 | Fink et al. | 600/443 |
| 5,456,113 A * | 10/1995 | Kwun et al. | 73/587 |
| 5,457,996 A | 10/1995 | Kondo et al. | |
| 5,487,306 A | 1/1996 | Fortes | |
| 5,581,037 A * | 12/1996 | Kwun et al. | 73/623 |
| 5,754,497 A * | 5/1998 | Tapia-Egoavil | 367/127 |
| 2001/0006435 A1* | 7/2001 | Ichihara et al. | 360/55 |
| 2001/0018891 A1* | 9/2001 | Loesch et al. | 117/200 |
| 2002/0158212 A1* | 10/2002 | French et al. | 250/459.1 |
| 2003/0176980 A1* | 9/2003 | Weiner et al. | 702/27 |
| 2004/0184361 A1* | 9/2004 | Ichihara et al. | 369/13.01 |

* cited by examiner

DEVICE AND METHOD FOR ANALYZING THE STRUCTURE OF A MATERIAL

This application is a §371 U.S. national stage application of PCT International Application No. PCT/FR02/03283, filed Sep. 26, 2002, claiming priority of French Application No. 01/12,516 filed Sep. 28, 2001, the contents of all of which is hereby incorporated herein by reference.

The invention relates to devices and methods for analyzing the structure of a material.

More precisely the invention relates to devices for analyzing the structure of a material, comprising:

- a probe comprising a plurality of probe elements for the emission of a wave, into the material, with an emission delay law corresponding to a deviation according to a direction and a focusing of this wave, and the reception, in parallel on the various probe elements, of signals originating from the refraction of this wave by the material,
- a plurality of emitters, each emitter exciting a single probe element,
- a plurality of detection channels, each detection channel being connected to a probe element, so as to: collect the refraction signals and transmit them to data processing means,
- a plurality of delay circuits, each delay circuit applying a delay, to each detection channel, according to a predetermined reception delay law corresponding to the deviation of the wave emitted.

Such analysis devices are already known. They are commonly used sequentially, as is illustrated by FIG. 1. The analysis is then performed by firing a shot, that is to say the emission of a wave by the whole set of probe elements according to a given deviation, for each desired exploration deviation. Each deviation corresponds: to a distinct delay law. The material is explored line by line by means of a moving beam, the exploration line being shifted between each shot.

Under these conditions, the time required to construct an image grows with the spatial resolution demanded, with the time of travel of the wave in the object analyzed and with the resolution of the reconstructed image. The analysis devices of this type do not in practice make it possible to exceed a few hundred hertz of image rate, this being hardly sufficient in numerous applications such as the inspection of sheet metal, tubes, track rails, etc.

An aim of the invention is to alleviate this drawback.

This aim is achieved, according to the invention, by an analysis device of the aforesaid kind in which each probe element emits the wave with at least one other emission delay law corresponding to the emission of the wave according to at least one other deviation, simultaneously, and the delay circuits apply delays, to each detection channel according to at least one other predetermined reception delay law corresponding to the reception of the wave emitted according to the other deviation. Specifically, the emission and reception delay laws used in the device according to the invention correspond to a plurality of deviations which, with the devices of the prior art, would have required as many shots as deviations, whereas the device of the invention analyzes the material according to various deviations, simultaneously, in a single shot.

In preferred embodiments of the device according to the invention, recourse is had to one and/or the other of the following arrangements;

- it comprises means of driving the delay circuits able to drive the delay circuits so as to process each wave according to a focusing varying as a function of time;
- it comprises means of digitization of the signal collected by each of the detection channels, with a sampling frequency lying between two and five times the frequency of emission of the probe elements, and preferably substantially equal to three times the frequency of emission of the probe elements;
- it comprises a digital interpolator with parallel outputs for multiplying the temporal resolution of the signal collected by each of the detection channels;
- the delay circuits comprise first delay cells and second delay cells in series and two summation circuits for summing the signals transmitted, after application of the delays respectively by the first and second delay cells;
- it comprises a linear amplifier for amplifying the amplitude of the wave prior to its emission by the probe elements; and
- the probe elements are laid out according to an arrangement chosen from among a linear arrangement, a matrix arrangement and a circular arrangement.

According to another aspect, the invention is a method of analyzing the structure of a material comprising:

- the emission of a composite wave consisting of a plurality of signals emitted by a probe comprising a plurality of probe elements, with an emission delay law corresponding to a deviation according to a direction and a focusing of this wave,
- the reception, in parallel, by the probe elements, of signals originating from the refraction of the wave, by the material,
- the transmission, by a plurality of detection channels, of the signals received by the probe elements, to data processing means,
- the application of a delay by delay circuits in parallel to each detection channel, according to a predetermined reception delay law corresponding to the deviation of the wave emitted, characterized in that it furthermore comprises the emission of at least one other wave, according to another deviation corresponding to another delay law, the emission of each wave being performed simultaneously, and in that the delay law corresponds to the simultaneous emission of the various waves, respectively according to each of the deviations.

In preferred modes of implementation of the method according to the invention, recourse is had to one and/or the other of the following arrangements:

- it comprises a digitization of the signals transmitted by each reception channel, with a sampling frequency lying between two and five times the frequency of emission of the probe elements, and preferably substantially equal to three times the frequency of emission of the probe elements.
- it comprises in succession the steps according to which:
- a first delay is applied to each signal corresponding to a detection channel,
- several signals corresponding to a group of probe elements are summed,
- a second delay is applied for each group, to each signal resulting from the above summation, and
- the delayed signals corresponding to the various groups are summed;

at least two different zones of the probe, each comprising a plurality of probe elements, simultaneously scan the material, according to all the deviations likewise simultaneously;

the signals received by the various probe elements are processed, in tandem with their reception, continuously, by the delay circuits; and the signals received by the various probe elements are stored in memory so as to be processed later by the delay circuits.

Other aspects, aims and advantages of the invention will become apparent on reading the detailed description which follows of one of its embodiments.

The invention will also be better understood with the aid of the references to the drawings in which:

FIG. 1 diagrammatically represents the various steps implemented, with a method of the prior art, to obtain an analysis of a material, according to three different deviations;

An exemplary embodiment of the device according to the invention is presented hereinbelow.

Figure 2:
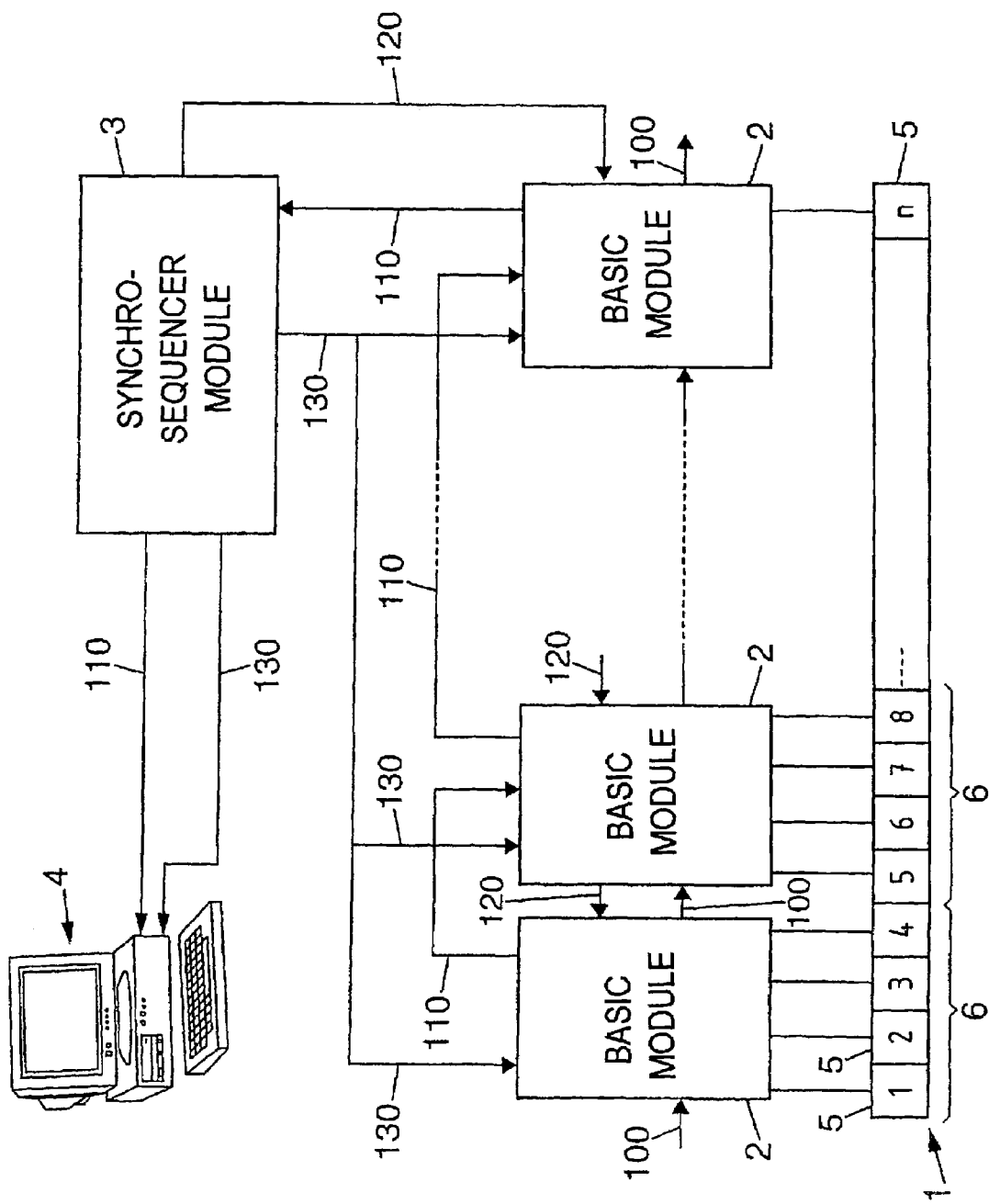
FIG. 2 is a general schematic of an embodiment of the device according to the invention.

According to this example, the device according to the invention, represented in FIG. 2, comprises a probe 1, basic modules 2, a synchro-sequencer module 3 and data processing means 4. The processing means 4 advantageously consist of a microcomputer.

The probe 1 consists of n probe elements 5. This number n is dependent on the desired application and/or on the technological limits of manufacture. By way of example, n=128. These n probe elements 5 are distributed in groups 6 of four consecutive probe elements 5, distributed over the probe 1. Each group 6 is processed by a basic module 2.

Each probe element 5 makes it possible to emit an ultrasound signal into a material and to detect, in return, the signal refracted by this material. Advantageously, each probe element 5 is of the piezo-composite type.

A basic module 2 communicates with the next basic module 2 by way of a summation bus 100 for summing the five deviations managed by each basic module 2.

The data collected by each basis module 2 are transferred to the next basic module 2 by way of a data bus 110 consisting of a high speed serial line. The last basic module 2 transfers all of the data obtained to the data processing means 4, via the synchro-sequencer 3, likewise by way of a data bus 110, consisting of a high speed serial line.

The synchro-sequencer module 3 has as its main function to interface the basic modules 2 and the processing means 4 and to generate synchronization signals on the basis of internal or external clocks, so as to transmit them to the basic modules 2 by way of a synchronization bus 120. In particular, the interfacing between the basic modules 2 and the processing means 4 comprises:

the storage, of the data detected, in a buffer memory, via a deserializer which recovers these data, originating from the basic modules 2, on the data bus 110;

the management of the transfers of these data to the processing means 4 via appropriate interfaces; and the tailoring of the parameters of the various basic modules 2, on the basis of the data originating from the data processing means 4.

The data processing means 4 communicate with each basic module 2, via the syncho-sequencer module 3, by way of an adjustment and configuration bus 130.

Figure 3:
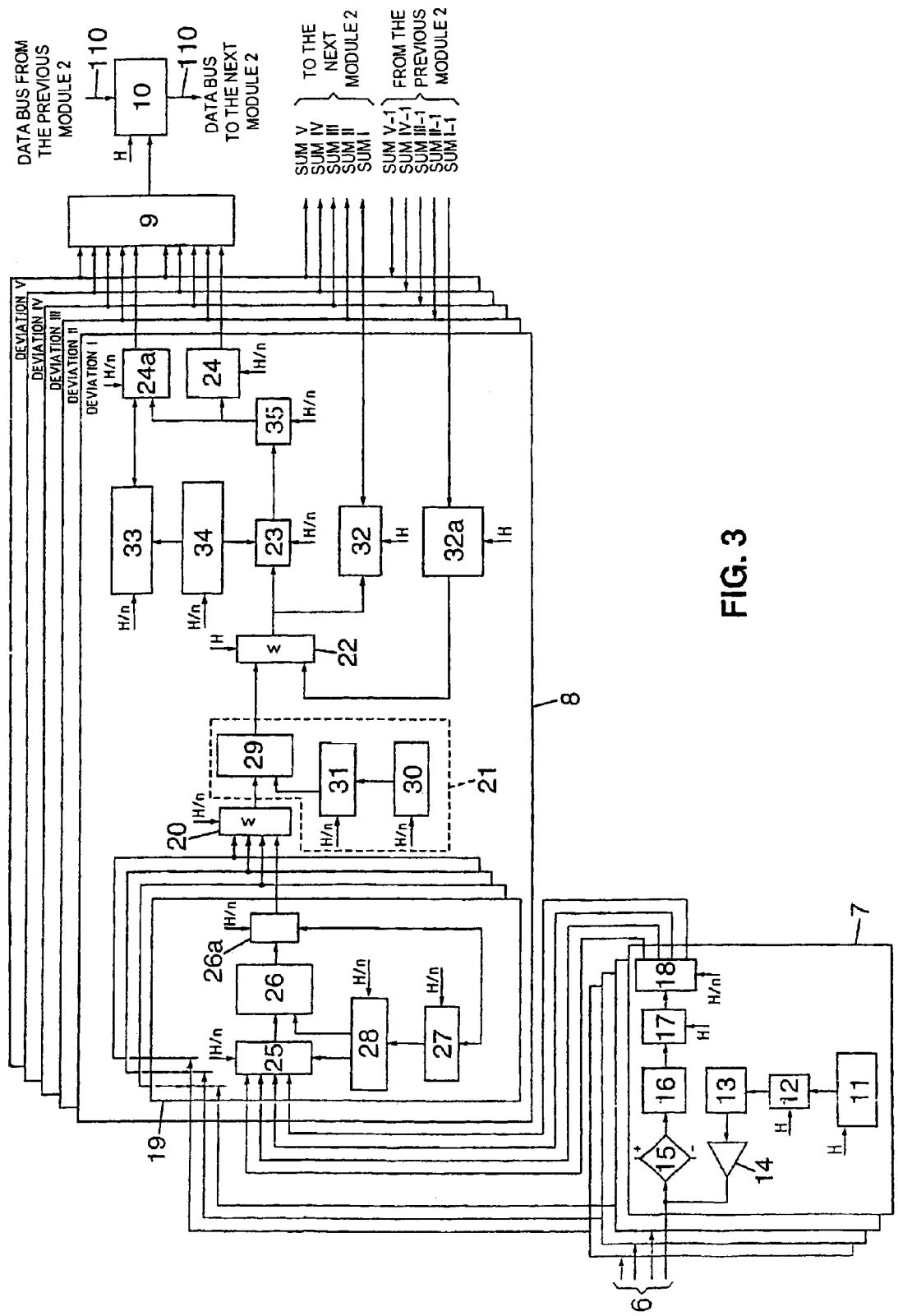
FIG. 3 is a schematic of a basic module of the embodiment of the device according to the invention represented in FIG. 2.

A basic module 2 is represented in greater detail in FIG. 3. Each basic module 2 comprises emission and reception means 7, delay circuits 8, a processor 9 and a transfer multiplexer 10.

Each basic module 2 comprises emission and reception means 7 four times, that is to say once per probe element 5.

Each basic module 2 comprises delay circuits 8 five times, that is to say once per deviation.

For each probe element 5, the emission and reception means 7 comprise, for emission, an emitter memory 11, a digital/analog converter 12, an analog low-pass filter 13 and an amplifier 14.

The emission and reception means 7 also comprise, for each probe element 5, for reception, a dipper 15, an analog filter 16, an analog digital converter 17 and a first digital interpolator 18 with parallel outputs.

Each basic module 2 has as its function to manage the four probe elements 5 of a group 6, as well as the emission of a compound wave corresponding to five different deviations I to V emitted by each probe element 5 of a group 6.

The management, by each basic module 2, of the probe elements 5 comprises, in particular:

the emission of ultrasounds,
the detection of ultrasound signals,
the analog/digital conversion of the signals detected, and
the digital interpolation of the signals detected, so as to increase the temporal resolution.

Figure 1:
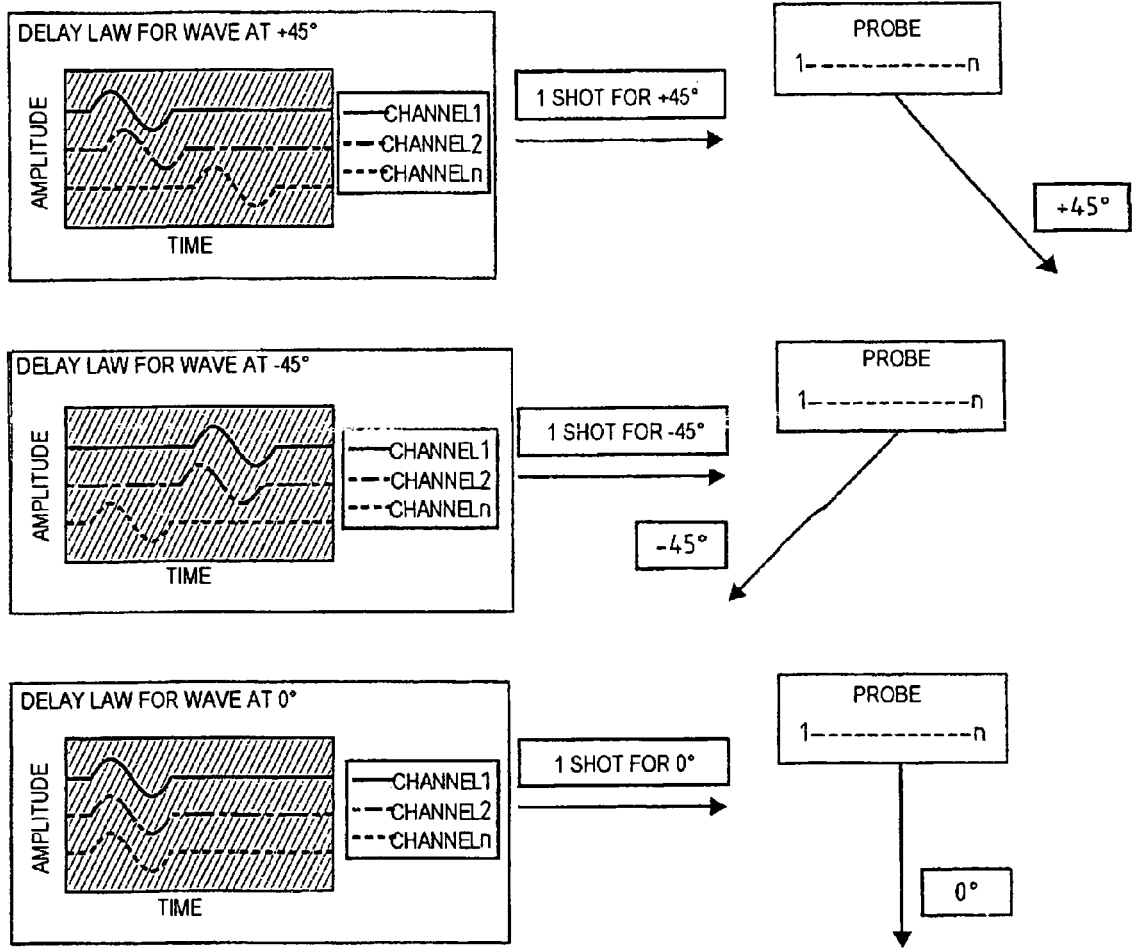
Figure 4:
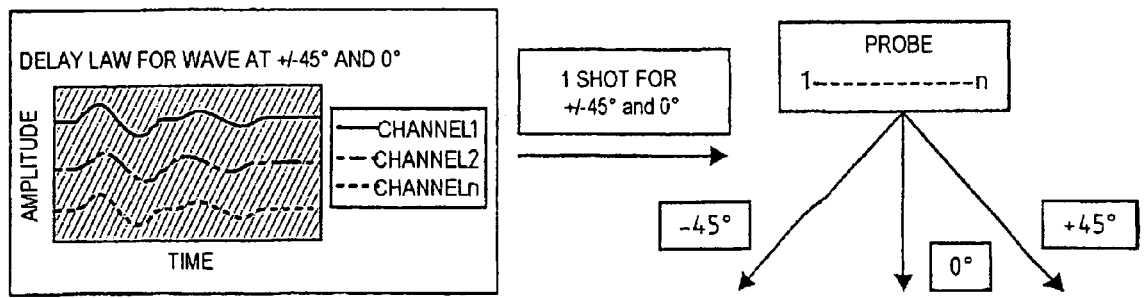
FIG. 4 diagrammatically illustrates the correspondence between the laws of delay and deviations of the wave emitted by the device corresponding to FIGS. 2 and 3.

For emission, emission curves are calculated in the phase of initialization of the device according, to the invention, with an accuracy ten times higher than the desired resolution. Each curve is constructed from the sum, according to emission delay laws, of the curves necessary for each of the five predetermined deviations of the ultrasound beam emitted by a given group 6. FIG. 4 illustrates, for three deviations (0 and plus or minus 45 degrees) the form of the delay law, that is to say the amplitude of the signal emitted by each probe element 5 as a function of time. These curves also take account of the apodization coefficients on emission which are intended to reduce the side lobes due to the spatial sampling of the probe 1.

These emission curves are sampled at a system frequency H. The corresponding sampled curves are then loaded into each emitter memory 11.

Thus, for example, for a 200 MHz probe, the accuracy of calculation of the curves should be 0.5 nanoseconds. The sampling frequency H may for its part be limited to around three times the frequency of the probe 1, i.e. 60 MHz. This is sufficient for correct reconstitution of the signal and has the advantage of limiting the hardware resources and hence the cost of the device according to the invention. By working with the lowest possible system frequency H it is possible to obtain large delays with a minimum of hardware resources.

In the firing phase, that is to say in the phase of emission of the wave by the probe 1, each emitter memory 11 is read out at the sampling frequency H. The digital data corresponding to the emission curves recorded in each emitter memory 11 of a channel corresponding to a given probe element 5, are converted, likewise at the sampling frequency H, after they have been read out, into analog signals by the digital/analog converter 12 of the same channel. The analog signal obtained is then filtered by the corresponding analog low-pass filter 13, in such a way as to reject the high-frequency components due to the sampling. The filtered signal is then amplified by the corresponding amplifier 14. This amplifier 14 is a linear power amplifier making it possible to provide the energy necessary for the excitation of a probe element 5.

The signals emitted by the various probe elements 5 into the material are refracted by the latter. These refracted signals are collected by each probe element 5. The dipper 15 protects the circuit elements 16, 17, 18 on input of the signals collected. The analog filter 16 then filters the signals so as to let through only the frequency components of the useful band. Finally, the signals are converted, at the frequency H/n, by the analog/digital converter 17, with a minimum dynamic range of 14 bits. This makes it possible to obtain an input dynamic range sufficient to avoid any analog gain control on input, and any saturation phenomenon. This dynamic range is also sufficient to process any of the deviations.

The first interpolator 18 performs, on the signal output by the analog digital converter 17, an interpolation by digital filtering, so as to obtain the temporal resolution necessary for the accuracy of the delay desired in order to perform the various deviations envisaged. Specifically, the system frequency H is, as we saw earlier, equal to around three times the frequency of the probe 1. This would not be sufficient to obtain the necessary resolution on first delay cells 19 which make up the delay circuits 8 and are situated downstream of the analog/digital converter 17, since this resolution is fixed at a tenth of the wavelength. However, the first interpolator 18 makes it possible to solve this problem by multiplying the temporal resolution by four, without raising the system frequency H. Thus, for a 20 MHz probe and a system frequency of 60 MHz, the resolution of the delay circuits of the delay circuits 8 is of the order of four nanoseconds.

The delay circuits 8 comprise, for each deviation I to V, a first delay cell 19, a first summator 20, a second delay cell 21, a second summator 22, as well as a multiplier circuit 23 and processing modules for utilization 24, 24a.

The delay circuits 8 manage, in particular:
the application, in parallel on the whole set of signals detected, delays according to reception delay laws corresponding to the various deviations desired,
weightings by apodization coefficients,
the digital summation in real time of the various signals delayed and weighted, so as to generate the signals corresponding to the various deviations desired;
the application of a gain to the delayed, weighted and summed signals.

On output from the first interpolator 18, for each probe element 5 and for each of the delay circuits 8, the first delay cell 19 manages the delays in a group 6 of four probe elements 5.

Each first delay cell 19 is made up of a multiplexer 25, of a first circular buffer circuit 26 and of a first divider circuit 26a. The multiplexer 25 selects the signals emanating from the emission and reception means 7 for each probe element 5 with the resolution of a tenth of the wavelength. The circular buffer circuit 26 applies a delay to each signal selected. The circular buffer circuit 26 makes it possible to obtain delays of several wavelengths by working at the frequency H/n. The first divider circuit 26a carries out an apodization in reception which reduces the side lobes due to the spatial sampling of the probe 1.

The first delay cell 19 is dynamically write-driven by a first memory circuit 27 and a second interpolator 28. The first memory circuit 27 stores, in the initialization phase, the characteristic points of the delay curve of the corresponding probe element 5. The second interpolator 28. regenerates the points intermediate to these characteristic points.

The first delay cell 19 has a resolution of the order of a tenth of the wavelength.

The first summator 20 adds together the signals emanating from the first delay cells 19 of each probe element 5 of a group 6, after they have been put in phase by the delays applied to them by the delay cells 19.

Each second delay cell 21 comprises a second circular buffer circuit 29. Each second delay cell 21 manages the delays between the groups 6. These delays may reach several hundred wavelengths. Each delay cell 21 is dynamically write-driven by a second memory circuit 30 and a third interpolator 31. The second memory circuit 30 stores, during the phase of initialization of the device according to the invention, the characteristic points of the delay curve of each group 6. The third interpolator 31 regenerates the points intermediate to the characteristic points. The second delay cell 21 operates, like the first delay cell 19, at the frequency H/n.

The second delay cell 21 has a resolution of the order of a third of the wavelength.

The second summator 22 adds the signals of a group 6, together with the signals originating from the previous group.

The transmission of the data for summation, by the second summator 22, between groups 6, is performed by high speed serial link through a serializer 32 and a deserializer 32a. Advantageously, these serial links make it possible to convey bit rates of the order of 1.5 G bytes/s. Advantageously also, the deserializers are of the LVDS type. (LVDS is the acronym standing for the expression "Low Voltage Differential Signaling"). These arrangements make it possible to preserve all the bits introduced by the first 20 and second 22 summators and to thus have a perfectly linear processing chain, with an output dynamic range of between 96 dB and 132 dB, for a probe 1 of 8 to 2043 probe elements 5.

The signal emanating from the summation by the second summator 22 has a gain applied to it by the multiplier circuit 23. The multiplier circuit 23 is driven dynamically by a third memory circuit 33 and a fourth interpolator 34. The third memory. circuit 33 stores the characteristic points of a gain curve. This gain curve has been stored in the third memory circuit 33 during the initialization phase. The fourth interpolator 34 generates the intermediate points between the characteristic points of the gain curve that are stored in the third memory circuit 33.

A fifth digital interpolator 35, with parallel output, makes it possible to retrieve the temporal resolution of the tenth of a wavelength without raising the system frequency H. This resolution is sufficient to permit all, the conventional processing performed by conventional apparatus for inspection and imaging by ultrasound. The data output by the fifth interpolator 35 are processed by the processing modules for utilization 24, 24a. These processing modules for utilization 24, 24a are advantageously respectively of the "echo display" (A-SCAN) type and "measurement of amplitudes and of distances in a selection window" (GATES) type. These processing modules for utilization 24, 24a are entirely conventional within the field of nondestructive inspection and imaging by ultrasound.

The signal resulting from the processing by the processing modules for utilization 24, 24a is dispatched by the processor 9 and the transfer multiplexer 10, to the next basic module 2 or to the data processing means 4, via a high speed serial link of LVDS type.

In the above described exemplary device according to the invention, the reception delay laws are applied, on the one hand, at the level of the first delay cells 19 and, on the other hand, at the level of the second delay cells 21. This makes it possible to have:

first delay cells 19 that can apply delays equal to, for example, forty times the length of the wave emitted into the material, with a relatively good resolution (for example of the order of a tenth of the wavelength); and second delay cells 21 that can apply delays equal to, for example, one hundred and sixty times the length of the wave emitted into the material, with a relatively low resolution (for example of the order of a third of the wavelength).

The device according to the invention allows the summation of signals that are out of phase by 0 to several hundred wavelengths, with a resolution of the order of a tenth of the wavelength. By virtue of the device according to the invention, deviations of the ultrasound beam emitted by the probe 1 of from 0 degrees to plus or minus 90 degrees are obtained, each deviation being, able to take any value whatsoever in this range independently of the values of the other deviations. The device according to the invention permitting moreover the frequency coding of the signals emitted for each deviation, the discrimination of the signs received is thereby greatly improved.

By way of example, for a 20 MH probe and hence a period of 50 nanoseconds, the out-of-phase span can vary from 0 to around 10 microseconds, with a resolution of five nanoseconds.

The delays are applied with an accuracy that is sufficient for it to be possible to abandon oversampling points so as to return to the volume and to the frequency of processing of the signals, before interpolation by the first interpolator 18.

The exemplary embodiment of the device presented above allows fully real time operation. The acquisition and processing rate depends only on the time of travel in the material analyzed, as in the conventional one-channel inspection systems, thereby permitting rates of several kilohertz in the majority of applications. This device comprises no acquisition memory, hence enabling substantial and unlimited durations of probing, without any cost overhead in hardware components for the analysis device. When the inspection conditions do not necessitate rates of several kilohertz, the device according to the invention can advantageously be associated with a head-end multiplexer which makes it possible to substantially reduce the overall cost of the analysis device. Moreover, the use of digital delay circuits allows angular deflections markedly greater than those obtained with analog circuits. Specifically, the accuracy of digital circuits does not depend on the absolute value of the delay.

The device according to the invention operates in a circular manner, that is to say emission and reception can be started and stopped on any probe element 5 whatsoever.

The above described device according to the invention allows the implementation of several methods likewise in accordance with the present invention.

According to a first exemplary method according to the invention, a composite wave made up of several signals emitted by the whole set of probe elements 5 of the probe 1 is emitted with emission delay laws allowing the simultaneous emission of the wave according to several deviations. The delay circuits 8 then process the signals corresponding to the wave emitted, which signals are refracted by the material and collected by the probe elements 5, while applying, to these signals, reception delay laws corresponding to the various deviations.

According to a second exemplary method according to the invention, a composite wave made up of several signals emitted simultaneously by at least two different zones of the probe 1 each comprising several probe elements 5 is emitted. Each of these zones then simultaneously scans the material to be analyzed, emitting the wave according to several deviations. We then process the signals refracted by the material and collected by the probe elements 5, zone by zone, applying reception delay laws to them corresponding to the various deviations of the wave emitted.

This second exemplary method is particularly advantageous. Specifically, for example by dividing the surface of the material to be analyzed into four regions and analyzing each of these regions with a different zone of the probe 1, the scanning rate is divided by four. If, with each of the zones, the wave is emitted according to five deviations, then a factor of twenty is gained in the rate of scanning of the material to be analyzed with respect to what could be obtained with the methods and devices of the prior art.

The device and the method according to the invention apply, not exclusively, to all inspections by ultrasound, namely, in the field of non destructive inspection, to portable apparatus and to automatic systems, and in the medical field, to diagnostic apparatus.

The device and the method according to the invention apply also to all systems which use a sensor consisting of a plurality of independent elements, whatever physical phenomenon is utilized: eddy currents, infrasound, electromagnetic waves, etc.

The device and the method according to the invention apply also to all multi-element sensors, be they linear, matrix-like or circular.

Numerous variants of the device and the method according to the invention may be envisaged with the embodiments and modes of implementation described above, without departing from the scope of the invention.

Thus, instead of the signals collected by the probe elements 5 being processed in real time, it is possible to provide for a buffer memory upstream of the delay circuits 8, so as to record these signals with a view to subsequent processing by these delay circuits 8.

Likewise, described herein above is a device comprising groups 6 of four probe elements 5, emitting according to five deviations, but the numbers of groups 6, of probe elements 5 per group 6 and of deviations is variable and depends on the applications and/or on the performance of the hardware components used for the manufacture of the device according to the invention.

The invention claimed is:

1. A device for analyzing the structure of a material, comprising:

a probe comprising a plurality of probe elements (5) for the emission of a wave, into the material, with an emission delay law corresponding to a deviation according to a direction and a focusing of this wave, and the reception, in parallel on the various probe elements (5), of signals originating from the refraction of this wave by the material, a plurality of emitters (7), each emitter (7) exciting a single probe element (5), a plurality of detection channels, each detection channel being connected to a probe element (5), so as to collect the refraction signals and transmit them to data processing means (4), a plurality of delay circuits (8), each delay circuit (8) applying a delay, to each detection channel, according to a predetermined reception delay law corresponding to the deviation of the wave emitted, characterized in that, each probe element (5) emits the wave with at least one other emission delay law corresponding to the emission of the wave according to at least one other deviation, simultaneously, and that the delay circuits apply delays to each detection channel according to at least one other predetermined reception delay law corresponding to the reception of the wave emitted according to the other deviation.

2. The device as claimed in claim 1, comprising means of driving the delay circuits (8) able to drive the delay circuits (8) so as to process each wave according to a focusing varying as a function of time.

3. The device as claimed in claim 1, comprising means of digitization (17) of the signal collected by each of the detection channels, with a sampling frequency lying between two and five times the frequency of emission of the probe elements (5), and preferably substantially equal to three times the frequency of emission of the probe elements (5).

4. The device as claimed in claim 1, comprising a digital interpolator (18) with parallel outputs for multiplying the temporal resolution of the signal collected by each of the detection channels.

5. The device as claimed in claim 1, in which the delay circuits (8) comprise first delay cells (19) and second delay cells (21) in series and two summation circuits (20, 22) for summing the signals transmitted, after application of the delays respectively by the first (19) and second (21) delay cells.

6. The device as claimed in claim 1, comprising a linear amplifier for amplifying the amplitude of the wave prior to its emission by the probe elements (5).

7. The device as claimed in claim 1, in which the probe elements (5) are laid out according to an arrangement chosen from among a linear arrangement, a matrix arrangement and a circular arrangement.

8. A method of analyzing the structure of a material comprising, the emission of a composite wave consisting of a plurality of signals emitted by a probe comprising a plurality of probe elements (5), with an emission delay law corresponding to a deviation according to a direction and a focusing of this wave, the reception, in parallel, by the probe elements (5), of signals originating from the refraction of the wave, by the material, the transmission, by a plurality of detection channels, of the signals received by the probe elements (5), to data processing means (4)

the application of a delay by delay circuits (8) in parallel to each detection channel, according to a predetermined reception delay law corresponding to the deviation of the wave emitted, characterized in that it furthermore comprises the emission of at least one other wave, according to another deviation corresponding to another delay law, the emission of each wave being performed simultaneously.

9. The method as claimed in claim 8, comprising a digitization of the signals transmitted by each reception channel, with a sampling frequency lying between two and five times the frequency of emission of the probe elements (5), and preferably substantially equal to three times the frequency of emission of the probe elements (5).

10. The method as claimed in claim 8, in which, all the deviations are processed in parallel and for each deviation, in succession, a first delay is applied to each signal corresponding to a detection channel, several signals corresponding to a group (6) of probe elements (5) are summed, a second delay is applied for each group (6), to each signal resulting from the above summation, and the delayed signals corresponding to the various groups (6) are summed.

11. The method as claimed in claim 8, in which at least two different zones of the probe (1), each comprising a plurality of probe elements (5), simultaneously scan the material, according to all the deviations likewise simultaneously.

12. The method as claimed in claim 8, in which the signals received by the various probe elements (5) are processed, in tandem with their reception, continuously, by the delay circuits (8).

13. The method as claimed in claim 8, in which the signals received by the various probe elements (5) are stored in memory so as to be processed later by the delay circuits (81).

* * * * *